(12) United States Patent
de Salazar Vinas

(10) Patent No.: US 7,713,057 B2
(45) Date of Patent: May 11, 2010

(54) ORAL MUCOUS MEMBRANE PROTECTOR FOR ORTHODONTIC APPLICATIONS

(76) Inventor: Maria Pilar de Salazar Vinas, Ramon Casas 1 1°A, Albacete (ES) 02006

( * ) Notice: Subject to any disclaimer, the term of this patent is extended or adjusted under 35 U.S.C. 154(b) by 91 days.

(21) Appl. No.: 10/599,126

(22) PCT Filed: Nov. 18, 2005

(86) PCT No.: PCT/ES2005/000631

§ 371 (c)(1),
(2), (4) Date: Sep. 20, 2006

(87) PCT Pub. No.: WO2006/075033

PCT Pub. Date: Jul. 20, 2006

(65) Prior Publication Data

US 2007/0218417 A1    Sep. 20, 2007

(30) Foreign Application Priority Data

Jan. 10, 2005   (ES)   .............................. 200500029 U
Mar. 22, 2005   (ES)   ................................ 200500666

(51) Int. Cl.
*A61C 3/00* (2006.01)
(52) U.S. Cl. .............................................. 433/17; 433/8
(58) Field of Classification Search ................. 433/2–24
See application file for complete search history.

(56) References Cited

U.S. PATENT DOCUMENTS 5,032,080 A  *  7/1991  Hakansson et al. ............. 433/8
5,766,005 A  *  6/1998  Casey .......................... 433/15
5,938,435 A       8/1999  Raspino, Jr.

\* cited by examiner

*Primary Examiner*—Ralph A Lewis
*Assistant Examiner*—Yogesh Patel
(74) *Attorney, Agent, or Firm*—Dennison, Schultz & MacDonald

(57) ABSTRACT

An oral mucous membrane protector for orthodontic appliances formed of a protective element or member arranged on the distal end of the archwire that projects from the molar tube, covering or enveloping the archwire and fixing it to the molar tube by means of an elastic ring joined to the protective element. The protective element may be reinforced on the bottom thereof so as to prevent tearing or perforation.

5 Claims, 2 Drawing Sheets

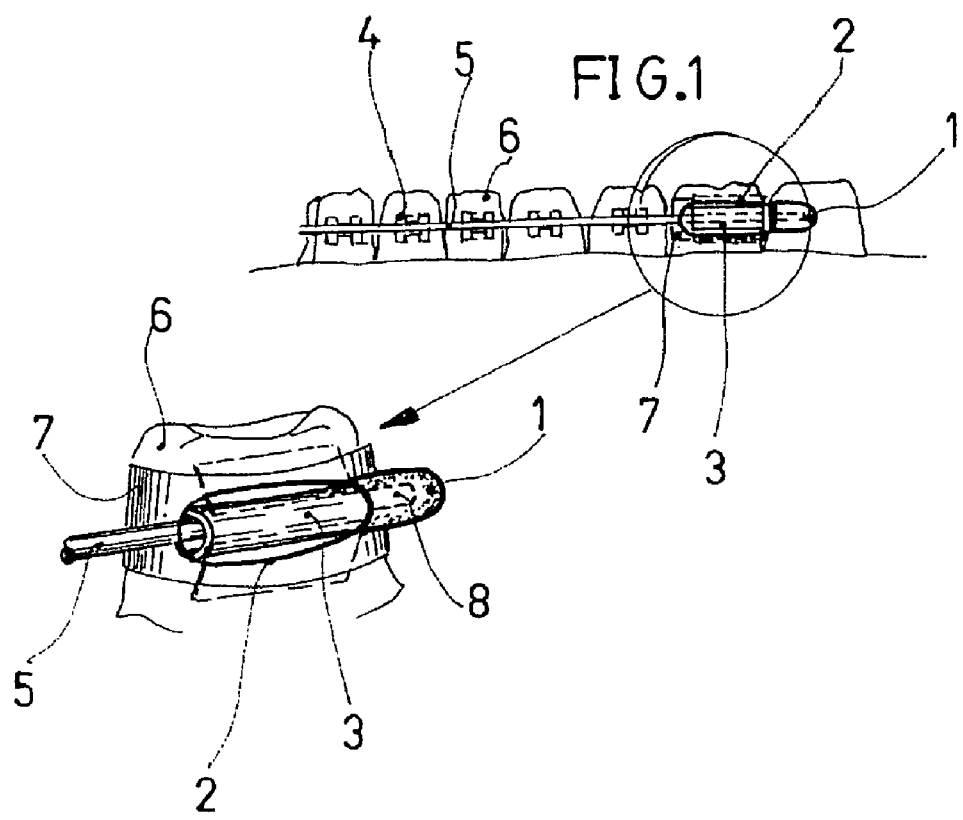
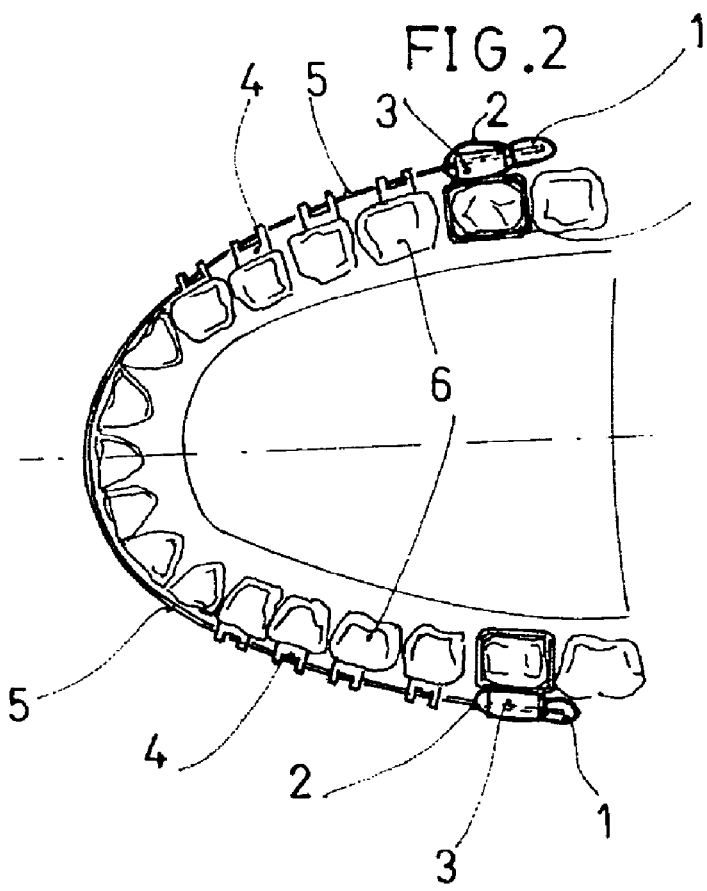

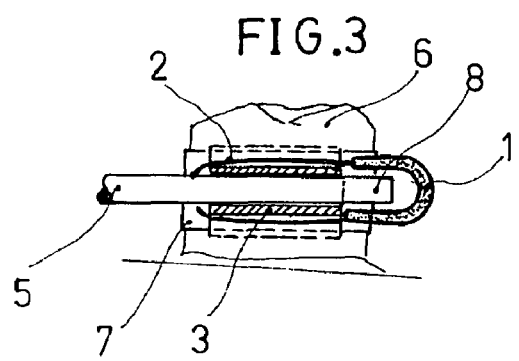
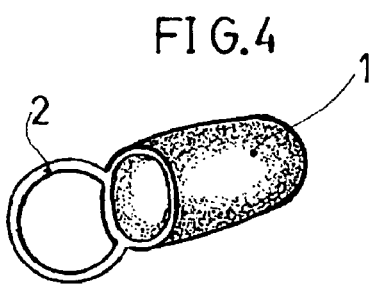
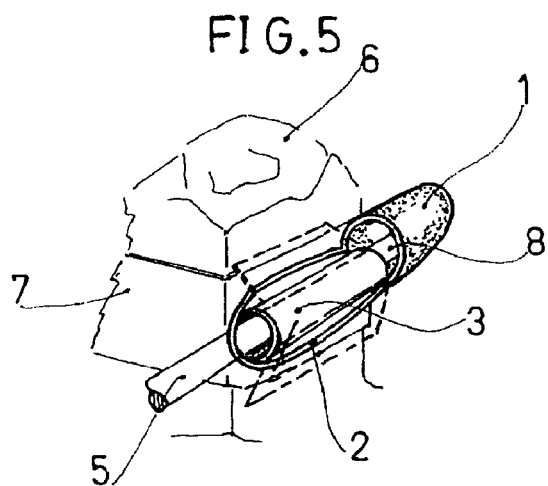
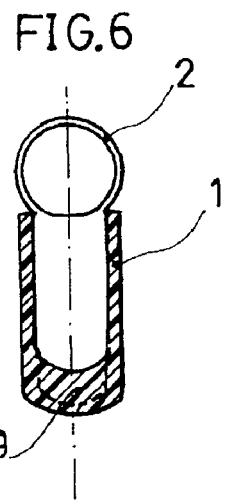

ORAL MUCOUS MEMBRANE PROTECTOR FOR ORTHODONTIC APPLICATIONS

BACKGROUND OF THE INVENTION

The present invention, improved oral mucous membrane protector for orthodontic appliances, relates to a new and original mucous membrane and lip protection device in certain orthodontic technique applications.

Therefore, the present invention is especially interesting for the field of the orthodontic branch of the odontological industry, and especially of orthodontic techniques.

Orthodontic treatments are currently widely known, which treatments are carried out by removable or fixed appliances or appliances cemented or attached to teeth as in the case of brackets, which can be metallic, ceramic or plastic. Braces and arch wires are common appliances in orthodontics; they are prescribed and designed by a professional according to the problem to be treated.

Treatments of this type are carried out applying a slight constant force in a controlled direction, and the appliances will move teeth slowly, through the bone sustaining them, towards the new desired position.

In some cases, orthodontic appliances, especially removable ones, direct forces for guiding jaw growth and development in children and teenagers (prevention treatment). For example, a "jaw expansion" apparatus can widen the upper jaw if it is narrow in only a couple of months.

Although in practice it is observed that there are is no protective material element for the ends of metallic orthodontic appliances and more specifically for the sharp distal end of the orthodontic archwire, there are background documents relating to orthodontic assemblies such as those contained in WO 2004069082 for "VERTICAL BUCAL TUBES WITH MALLEABLE ARRESTING FLAPS", in the name of De Simone Pasquale (IT); EP 1360941 A1 for "ZAHNSPANGE" (DENTAL BRACES), in the name of Weissbach Otte K. and WO 021091940 A1, for "SUTURE EXPANSION DEVICE", in the name of Van Straten Research & Development B.V., and more specifically to the recent U. 200500029 for "ORAL MUCOUS MEMBRANE PROTECTOR FOR ORTHODONTIC APPLICATIONS" of the same inventor and the same applicant of this specification corresponding to a simple version which does not deal with or specify the structural expression, the correct constructive version and the material factor which are developed in the object of this patent.

Nevertheless and despite the benefits, these treatments imply a series of discomforts for the patient. For example, patients who have brackets and wires must take care to not eat hard foods or bite objects because this makes the appliances fall or become deformed, delaying the treatment.

Likewise the tendency to accumulate bacterial plaque is greater in teeth with appliances because these retain more food remains, therefore hygiene must be meticulous otherwise the gums will inflame and cavity formation will be imminent and then the treatment will have to be stopped in order to solve these problems, and this would increase the time and costs.

Lips, cheeks and tongue can also be irritated for one or two weeks while they get used to the appliances and therefore they become inflamed; this situation ends quickly without any major consequences.

To this respect, there are two main techniques to prevent the distal parts of orthodontic archwires from pricking the jugal mucous membrane (cheek mucous membrane).

On one hand, orthodontic wax can be used. This is supplied in easily applicable wax bars, by means of molding it and placing it covering the end of the arch projecting from the tube, as well as any other metallic element of the brace system, for the purpose of preventing contact with the mucous membranes and the damage thereof.

The other system consists of the use of distal cutting pliers. These are special pliers for cutting that part projecting from the arch at the level of the distal end of the molar tube. Nevertheless, there are three circumstances in which this is not effective. The first is when the arches are thin (of a small profile) and they move towards one of the sides, making them prick the mucous membrane of one side and disengaging from the molar tube on the opposite side. The second situation is when dental retrusion movements occur, in which the length of the dental arch decreases, leaving extra archwire on both sides of the arch and pricking the mucous membrane bilaterally. The third situation is when the molar is rotated, the distal part of the molar tube is directly facing the cheek mucous membrane and although the archwire is cut at the level of the tube, it pricks the mucous membrane.

SUMMARY OF THE INVENTION

The present invention satisfactorily solves the previous drawbacks and therefore, it implies an important progress in the state of the art, providing a simple and comfortable solution of wide use in patients suffering from this type of treatments.

In view of the above, the present improved oral mucous membrane protector for orthodontic applications described below is mainly and essentially formed by a structure of a protective element or member, susceptible of being fixed to a bracket system surrounding the molar tube, behind its flaps, at the height of the arch projecting from the tube at the distal end and covering, enveloping and protecting the distal end of the arch. The mentioned protective element or member is fixed to the cited brace system in the molar tube behind the flaps, which acts functionally as a receiver of the end of the arch and guide thereof.

On the other hand, the mentioned protective element or member is formed by two functional parts, one part for fixing on the molar tube behind the flaps of the bracket structure where the end of the archwire is, and a cover or cap for covering the mentioned distal end of the archwire and for protecting the mucous membranes inside the mouth. Said fixing of the cover or cap is formed by an elastic ring integral therewith.

Likewise, the ring part for fixing to the molar tube of the bracket system embraces the molar tube behind the flaps which exists for the guiding of said fixing archwire the end of which is covered with the mentioned cover or cap for protecting the mucous membranes inside the mouth.

On the other hand, the mentioned cover or cap for covering the mentioned end of the archwire and for protecting the mucous membranes inside the mouth is preferably made of synthetic, elastic, impermeable and soft material, for example a silicone or solid gel, so it can be adapted to the length of the distal end of the archwire to be covered. Furthermore, said cover or cap for covering the mentioned end of the archwire and for protecting the mucous membranes can also be reinforced in its interior, in the bottom part, by a reinforcement formed by thickening the material itself or another suitable material, thus increasing its resistance to being torn or perforated by the sharp distal end of the archwire.

BRIEF DESCRIPTION OF THE DRAWINGS

A detailed description of the oral mucous membrane protector which is the object of the present invention will be carried out below with reference to the attached drawings which show, by way of a non-limiting example, a preferred embodiment susceptible of all those detail variations which do not imply a fundamental alteration of the essential features of said improvements.

Said drawings illustrate:

FIG. 1 shows a side elevational view of an orthodontic assembly for the oral mucous membrane protector for orthodontic applications object of the invention and an enlarged detail of the application.

FIG. 2 shows an upper plan view of the representation of the previous figure at Figure 90° therefrom.

FIG. 3 shows a sectional view of the enlarged detail of FIG. 1.

FIG. 4 shows a horizontal perspective view of the cover or cap according to the invention.

FIG. 5 shows a perspective view of the protective cover or cap assembled on the molar tube in a normal application projection.

FIG. 6 shows a sectioned view of FIG. 4 in a vertical position of the cover or cap reinforced at the bottom thereof.

DESCRIPTION OF THE PREFERRED EMBODIMENTS

According to the depicted embodiment, the oral mucous membrane protector for orthodontic applications shown in this preferred embodiment is essentially formed by a structure (1) of synthetic, elastic, impermeable and soft material, for example a silicone or solid gel, a protective element or member susceptible of being fixed to a bracket system (4) surrounding the molar tube (3) behind its flaps, at the height of the archwire (5) projecting from the distal end (8) of the molar tube (3) that is joined to the band (7) of the molar (6), covering and enveloping the end (8) of the archwire (5). The mentioned protective element or member (1) is fixed to the mentioned bracket system (4) by means of a ring (2), and more specifically in the molar tube (3), functionally acting as a guide of the distal end (8) of the archwire (5), potentially isolating it from the mucous membranes susceptible of being damaged inside the patient's mouth.

On the other hand the mentioned protective element or member (1) is formed by two functional parts, one part (2) for fixing on the molar tube (3) of the bracket system (4), where the end (8) of the archwire (5) is and for protecting the mucous membranes inside the mouth, said fixing (2) of the cover or cap (1) being formed by a ring of elastic material or rubber joined thereto.

On the other hand, the mentioned cap or cover (1) for covering the mentioned distal end (8) of the archwire (5) and protecting the mucous membranes inside the mouth, of the mentioned elastic material, can be adapted to the length of the end (8) of the archwire (5) to be covered and protected. Said cap or cover (1) for covering the mentioned end (8) of the archwire (5) and for protecting the mucous membranes can further be reinforced (9) in its interior, at the bottom part, with an optional reinforcement, even of the same material, thus increasing its resistance to being torn or perforated by the sharp end (8) of the archwire (5).

Finally, the shape, materials and sizes may vary and generally so may any accessory and secondary aspect provided that it does not change or modify the essential feature of the improvements that have been described.

The invention claimed is:

1. In an orthodontic appliance adapted to be disposed in the mouth of a patient, comprising a molar tube, and an archwire having an end projecting from a distal end of the molar tube, wherein the improvement comprises an oral mucous membrane protector comprising:
a cap having a closed end and an open end surrounded by a wall, the end of the archwire being received in the open end, and
an elastic ring integral with and projecting from the wall in a direction opposite to the closed end and fixed around the molar tube to secure the cap over the archwire, the elastic ring projecting from a portion of the wall such that the elastic ring does not block the open end of the cap,
wherein the protector isolates mucous membranes susceptible of being damaged inside the mouth, and preventing disengagement of the archwire from the molar tube.

2. An appliance according to claim 1, wherein the protective element is made of a synthetic, elastic, impermeable and soft material.

3. A appliance according to claim 1, wherein the cap is made of a silicone or solid gel.

4. An appliance according to claim 1, wherein an internal reinforcement of the cap is provided at the closed end.

5. An appliance according to claim 4, wherein the internal reinforcement is made of the same material as the cap.

* * * * *